(12) United States Patent
Low et al.

(10) Patent No.: US 8,168,164 B2
(45) Date of Patent: May 1, 2012

(54) TARGETED CONJUGATES AND RADIATION

(75) Inventors: Philip Stewart Low, Glenview, IL (US); Emanuela Ionela Sega, West Lafayette, IN (US)

(73) Assignee: Purdue Research Foundation, West Lafayette, IN (US)

(*) Notice: Subject to any disclaimer, the term of this patent is extended or adjusted under 35 U.S.C. 154(b) by 0 days.

(21) Appl. No.: 12/162,661

(22) PCT Filed: Feb. 2, 2007

(86) PCT No.: PCT/US2007/002865
§ 371 (c)(1),
(2), (4) Date: Jul. 30, 2008

(87) PCT Pub. No.: WO2007/092299
PCT Pub. Date: Aug. 16, 2007

(65) Prior Publication Data
US 2008/0317706 A1    Dec. 25, 2008

Related U.S. Application Data

(60) Provisional application No. 60/764,996, filed on Feb. 3, 2006.

(51) Int. Cl.
*A61K 39/00* (2006.01)

(52) U.S. Cl. .............. 424/85.2; 424/130.1; 424/193.1

(58) Field of Classification Search .......................... None
See application file for complete search history.

(56) References Cited

U.S. PATENT DOCUMENTS

| 2,816,110 | A | 12/1957 | Sletzinger et al. |
|---|---|---|---|
| 4,659,655 | A | 4/1987 | Rose |
| 4,713,249 | A | 12/1987 | Schroder |
| 5,057,540 | A | 10/1991 | Kensil et al. |
| 5,075,287 | A | 12/1991 | Hasegawa |
| 5,108,921 | A | 4/1992 | Low et al. |
| 5,117,022 | A | 5/1992 | Khokhar et al. |
| 5,137,720 | A | 8/1992 | Gangemi et al. |
| 5,140,104 | A | 8/1992 | Coughlin et al. |
| 5,266,333 | A | 11/1993 | Cady et al. |
| 5,273,965 | A | 12/1993 | Kensil et al. |
| 5,416,016 | A | 5/1995 | Low et al. |
| 5,417,982 | A | 5/1995 | Modi |
| 5,443,829 | A | 8/1995 | Kensil et al. |
| 5,508,310 | A | 4/1996 | Rhodes |
| 5,547,668 | A | 8/1996 | Kranz et al. |
| 5,552,545 | A | 9/1996 | Pearce et al. |
| 5,583,112 | A | 12/1996 | Kensil et al. |
| 5,583,202 | A | 12/1996 | Zanetti |
| 5,602,171 | A | 2/1997 | Tang et al. |
| 5,635,382 | A | 6/1997 | Low et al. |
| 5,650,398 | A | 7/1997 | Kensil et al. |
| 5,672,486 | A | 9/1997 | Soulillou |
| 5,688,488 | A | 11/1997 | Low et al. |
| 5,747,024 | A | 5/1998 | Grabstein et al. |
| 5,820,847 | A | 10/1998 | Low et al. |
| 5,932,208 | A | 8/1999 | Chedid et al. |
| 5,977,081 | A | 11/1999 | Marciani |
| 6,080,725 | A | 6/2000 | Marciani |
| 6,231,859 | B1 | 5/2001 | Kensil |
| 6,262,029 | B1 | 7/2001 | Press et al. |
| 6,291,673 | B1 | 9/2001 | Fuchs et al. |
| 6,335,434 | B1 | 1/2002 | Guzaev et al. |
| 7,033,594 | B2 * | 4/2006 | Low et al. .................. 424/193.1 |
| 2002/0039583 | A1 | 4/2002 | Subjeck et al. |
| 2003/0086900 | A1 | 5/2003 | Low et al. |
| 2003/0198643 | A1 | 10/2003 | Lu |
| 2005/0002942 | A1 | 1/2005 | Vlahov et al. |
| 2006/0067946 | A1 | 3/2006 | Low et al. |
| 2007/0037764 | A1 | 2/2007 | Mourich et al. |

FOREIGN PATENT DOCUMENTS

| EP | 0220030 A2 | 4/1987 |
|---|---|---|
| EP | 217577 | 8/1987 |
| JP | 64-79125 | 3/1989 |
| JP | 3-173814 | 7/1991 |
| WO | WO 85/04808 | 11/1985 |
| WO | WO 91/07418 | 5/1991 |
| WO | WO91/11146 | 8/1991 |
| WO | WO 96/36367 | 11/1996 |
| WO | WO97/37690 | 10/1997 |
| WO | WO 97/41831 | 11/1997 |
| WO | WO 00/10599 | 3/2000 |
| WO | WO 00/74721 | 12/2000 |
| WO | WO 01/12172 | 2/2001 |
| WO | WO 01/12840 | 2/2001 |
| WO | WO 01/22972 | 4/2001 |
| WO | WO 01/22990 | 4/2001 |
| WO | WO 01/32207 | 5/2001 |
| WO | WO 01/47552 | 7/2001 |
| WO | WO 01/51083 | 7/2001 |

(Continued)

OTHER PUBLICATIONS

Gridley et al (Cancer Therapy, 2005, 3:105-130).*

(Continued)

*Primary Examiner* — Laura B Goddard
(74) *Attorney, Agent, or Firm* — Barnes & Thornburg LLP

(57) ABSTRACT

The invention relates to a method for enhancing an endogenous immune response-mediated elimination of a population of cancer cells in a host. The method comprises the steps of administering to the host a composition comprising an immunogen conjugated to a vitamin receptor-binding ligand selected from the group consisting of a vitamin, or an analog or a derivative thereof, and administering to the host a therapeutically effective amount of radiation wherein the amount of radiation can range from about 0.5 to about 10 Gy per dose.

25 Claims, 6 Drawing Sheets

FOREIGN PATENT DOCUMENTS

WO     WO 01/74382     10/2001

OTHER PUBLICATIONS

Demaria et al (Int J Radiation Oncology Biol Phys, 2005, 63:655-666).*
Lu et al (Advanced Drug Delivery Reviews, 2004, 56:1161-1176).*
Friedman (Current Pharmaceutical Design, 2002, 8:1765-1780).*
Younes et al (Cellular Immunology, 1995, 165:243-251).*
Hillman et al, Clinical Cancer Research, 2001, 7:136-144.*
Triest et al, Clinical Cancer Research, 1998, 4:2009-2014.*
Kennedy, Michael D., et al., "Evaluation of Folate Conjugate Uptake and Transport by the Choroid Plexus of Mice", May 2003, *Pharmaceutical Research*, vol. 20, No. 5, pp. 714-719.
Livingston, Philip, "Section 23.5 Immunization With Synthetic or Highly Purified Tumor Antigens", *Biologic Therapy of Cancer: Principles and Practice*, J. B. Lippincott Company, 1995, pp. 680-689.
International Search Report/Written Opinion for PCT/US2007/002865 completed Jul. 17, 2008.
Mirzale-Joniani, Homa, et al., "Apoptosis Induced by Low-Dose and Low-Dose-Rate Radiation", *Supplement to Cancer: Eighth Conference on Radioimmunodetection and Radioimmunotherapy for Cancer*, American Cancer Society, 2002, pp. 1210-1214.
Sega, Emanuela I., et al., "Low-Dose Radiation Potentiates the Therapeutic Efficacy of Folate Receptor-Targeted Hapten Therapy", *International Journal Radiation Oncology; Biology; Physics*, 2008, vol. 71, No. 2, pp. 559-566.
U.S. Appl. No. 60/988,621, filed Nov. 16, 2007, Leamon et al.
George et al., "Redirection of T cell-mediated cytotoxicity by a recombinant single-chain Fy molecule", *Journal of Immunology*, 152: 1802-1811 (1994).
Berd et al., "Immunization with haptenized, autologous tumor cells induces inflammation of human melanoma metastases". *Cancer Research*. 51: 2731-2734 (1991).
Link Jr. et al., "Eliciting hyperacute xenograft response to treat human cancer: α(1,3) galatosyltransferase gene therapy."*Anticancer Research*. 18: 2301-2308 (1998).
Ben-Efraim et al., "Use of xenogenized tumor cells for treatment in experimental tumor and in human neoplasia". *Biomed. & Pharmacother.* 54: 268-273 (2000).
Olsnes et al., "Immunotoxins—Entry into cells and mechanisms of action," *Immunology Today*, 10(9): 291 (1989).
Melby et al., "Entry of protein toxins in polarized epithelial cells", *Cancer Research*, 53: 1755-1760 (1993).
Lussow et al., "Redirecting circulating antibodies via ligand-hapten conjugates eliminates target cells in vivo". *Journal of Immunotherapy.* 19(4):257-265 (1996).
Lussow et al., "Targeting of antihapten antibodies to activated T cells via an IL-2-hapten conjugate prolongs cardiac craft survival". *Transplantation*. 62(12): 1703-1708 (1996).
Roy et al., "Targeting T cells against brain tumors with a bispecific ligand-antibody conjugate", *Int J. Cancer*, 76: 761-766 (1998).
U.S. Appl. No. 60/990,815, filed Nov. 28, 2007, Leamon et al.
U.S. Appl. No. 61/003,212, filed Nov. 15, 2007, Leamon et al.
U.S. Appl. No. 61/043,833, filed Apr. 10, 2008, Leamon et al.
Patrick, et al., "Intracerebral bispecific ligand-antibody conjugate increases survival of animals bearing endogenously arising brain tumors". Int. J. Cancer. 78: 470-479 (1998).
Guyre et al., "Increased potency of Fc-receptor-targeted antigens", Cancer Immunol. Immunotherapy, 45: 146-149 (1997).
Lanza et al., Use of antigenized antibodies containing CD4 sequences to generate antibodies able to inhibit syncytia formation. FASEB J., Abstract No. 2690. p. A1400 (1992).
K. Hasegawa et al., "Composite Immunological Antibiotic (Abstract of CN 1044781C), published Aug. 22, 1990.
Roberts et al., "Folic acid analogs. Modifications in the benzene-ring region. 3. Neohomofolic and neobishomofolic acids. Improved synthesis of folic acid and its analogs". Journal of Medical Chemistry, 16:697-699 (1973).
Roberts et al., "Folic acid analogs. Modifications in the benzene-ring region. 2. Thiazole analogs", Journal of Medical Chemistry. 15: 1310-1312 (1972).
Roberts et al., "Folic acid analogs. Modifications in the benzene-ring region. 1. 2'- and 3'-Azafolic acids", Journal of Medical Chemistry. 14: 125-130 (1971).
Weinstock et al., "Folic acid analogs. II. p-{[(2,6-Diamino-8-purinyl)methyl]amino}-benzoyl-L-glutamic acid and related compounds", Journal of Medical Chemistry, 13: 995-997 (1970).
Drummond et al., "Liposome targeting to tumors using vitamin and growth factor receptors", Vitamins and Hormones. 60: 285-332 (2000).
Bock et al., "Sulfonamide structure-activity relations in a cell-free system. 2. Proof for the formation of a sulfonamide-containing folate analog". Journal of Medical Chemistry. 17: 23-28 (1974).
Roberts et al., "Folic acid analogs. Modifications in the benzene-ring region. 4. 3'-Ethyl- and 3'-isopropylfolic acids". Journal of Medical Chemistry. 17: 219-222 (1974).
Lee et al., "Folic acid antagonists. Methotrexate analogs containing spurious amino acids. Dichlorohomofolic acid". Journal of Medical Chemistry. 17: 326-330 (1974).
Kim et al., "Synthesis and biological activity of 10-thia-10-deaza analogs of folic acid, pteroic acid, and related compounds". Journal of Medical Chemistry. 18: 776-780 (1975).
Nair et al., "Folate analogues altered in the C9-N10 bridge region. 10-Oxafolic acid and 10-oxaaminopterin", Journal of Medical Chemistry. 19: 825-829 (1976).
Plante et al., "Polyglutamyl and polylysyl derivatives of the lysine analogs of folic acid and homofolic acid", Journal of Medical Chemistry. 19: 1295-1299 (1976).
Hynes et al., "Quinazolines as inhibitors of dihydrofolate reductase. 4. Classical analogs of folic and isofolic acids", Journal of Medical Chemistry, 20: 588-591 (1977).
Oatis et al., "Synthesis of quinazoline analogs of folic acid modified at position 10", Journal of Medical Chemistry. 20. 1393-1396 (1977).
Nair et al., "Folate analogs altered in the C9-N10 bridge region: N10-tosylisohomofolic acid and N10-tosylisohomoaminopterin". Journal of Medical Chemistry. 21: 673-677 (1978).
Nair et al., "Folate analogs altered in the C9-N10 bridge region: 11-thiohomofolic acid", Journal of Medical Chemistry. 22: 850-858 (1979).
Nair et al., "Folate analogs altered in the C9-N10 bridge region. 14. 11-Oxahomofolic acid, a potential antitumor agent". Journal of Chemistry. 23: 59-65 (1980).
Nair et al., "Folate analogs altered in the C9-N10 bridge region. 18. Synthesis and antitumor evaluation of 11-oxahomoaminopterin and related compounds". Journal of Medical Chemistry. 24: 1068-1073 (1981).
Temple et al., "Synthesis of pseudocofactor analogs as potential inhibitors of the folate enzymes", Journal of Medical Chemistry. 25: 161-166 (1982).
Nair et al., "Folate analogs. 20. Synthesis and antifolate activity of 1',2',3',4',5',6'-hexahydrohomofolic acid", Journal of Medical Chemistry. 26: 135-140 (1983).
Nair et al., "Folate analogs. 21. Synthesis and antifolate and antitumor activities of N10-(cyanomethyl)-5,8-dideazafolic acid", Journal of Medical Chemistry, 26: 605-607 (1983).
Nair et al., "Folate analogs. 22. Synthesis and biological evaluation of two analogs of dihydrofolic acid possessing a 7,8-dihydro-8-oxapterin ring system". Journal of Medical Chemistry. 26: 1164-1198 (1983).
Leamon et al. "Selective targeting of malignant cells with cytotoxin-folate conjugates," J. of Drug Targeting, 2: 101-12 (1994).
Reddy et al., "Expression and functional characterization of the B-isoform of the folate receptor on CD34+ cells." Blood. 93: 3940-3948 (1999).
Reddy et al., "Folate-Mediated Targeting of Therapeutic and Imaging Agents to Cancers," Critical Reviews in Therapeutic Drug Carrier Systems. 15(6). 587-627 (1998).
Kranz et al., "Conjugates of folate and anti-T-cell-receptor antibodies specifically target folate-receptor-positive tumor cells for lysis." Proc. Natl. Acad. Sci. USA. vol. 92. pp. 9057-9061. Sep. 1995.
Cho et al., "Single-Chain Fv/Folate Conjugates Mediate Efficient Lysis of Folate-Receptor-Positive Tumor Cells." Bioconjugate Chem., vol. 8. 338-346 (1997).

Ward et al., "Folic Acid Targeting of Protein Conjugates into Ascites Tumour Cells from Ovarian Cancer Patients." Journal of Drug Targeting. vol. 8. No. 2. 119-123 (2000).
Mastrangelo et al., "Active Specific Immunization in the Treatment of Patients With Melanoma," Seminars in Oncology, vol. 23, No. 6, 773-781 (Dec. 1996).
Rihova et al., Polymeric drugs based on conjugates of synthetic and natural macromolecules. II. Anti-cancer activity of antibody or (Fab')2-targeted conjugates and combined therapy with immunomodulators. Journal.
Blanka Rihova, "Receptor-mediated targeted drug or toxin delivery," Advanced Drug Delivery Reviews, 29, 273-289 (1998).
Richard A. Insel, "Potential Alterations in Immunogenicity by Combining or Simultaneously Administering Vaccine Components." Annals New York Academy of Sciences. 35-47.
Kim et al., "Comparison of the effect of different immunological adjuvants on the antibody and T-cell response to immunization with MUC1-KLH and GD3-KLH conjugate cancer vaccines." Vaccine. vol. 18.
Pisetsky, "Immune Activation by Bacterial DNA: A New Genetic Code," Immunity, vol. 5, 303-310, Oct. 1996.
Database Medline on STN, US National Library of Medicine, No. 2000143207, C. P. Leamon et al., "Folate-Mediated Drug Delivery: Effect of Alternative Conjugation Chemistry." Abstract. Journal of Drug.
Database Medline on STN, US National Library of Medicine, No. 1979:551180, Strominger et al., "Drug-Receptor Interactions: The Example of Beta-Lactam Antibodies." Abstract. Adv. Pharmacol. Ther. Proc. Int.
Database Medline on STN, US National Library of Medicine, No. 1999434114, D.J. Easty et al., "Up-Regulation of Ephrin-A1 During Melanoma Progression," Abstract, International Journal of Cancer, Oct. 22, 1999, vol. 84, No. 5, pp. 494-501.
Database Medline on STN, US National Library of Medicine, No. 2000013158, J. Walker-Daniels et al., "Overexpression of the EphA2 Tyrosine Kinase in Prostate Cancer," Abstract, Prostate, Dec. 1, 1999, vol.
Database Medline on STN, US National Library of Medicine, No. 2001:267809; S. Kremlev et al., Macrophage-Mediated Inflammation in Experimental Autoimmune Neuritis: The Role of the Integrin and.
Database Medline on STN, US National Library of Medicine, No. 89271983, T. Hamaoka, "Future Perspectives on Tumor-Specific Immunotherapy Using Hapten-Reactive T Cell Activity," Abstract. Gan to.
Abstract of Mazzoni et al., Proc. Annu. Meet. Am. Assoc. Cancer Res., 38: A558 (1997).
Midoux et al., "Activation of Mouse Macrophage by Muranyl Dipeptide Coupled with an Anti-Macrophage Monoclonal Antibody." Bioconjugate Chem., 3:194-199 (1992).
Vidal et al., Macrophage Stimulation with Murabutide, an HIV-Suppressive Muramyl Peptide Derivative, Selectivity Activates Extracellular Signal-Regulated Kinases 1 and 2. C/EBPβ and STAT1: Role of CD14.
Aderem & Ulevitch, "Toll-like Receptors in the Induction of the Innate Immune Response," Nature, 406:782-787 (2000).
Park & Bendelac, "CD1-Restricted T-Cell Responses and Microbial Infection," Nature, 406:788-792 (2000).
Akira et al., "Toll-like Receptors: Critical proteins linking innate and acquired immunity," Nature Immunology. 2:675-680 (2001).
Low, Philip S., Lu, Yinguan; "Folate-mediated targeting of imaging and immunotherapeutic agents to tumors in vivo." Proceedings of the American Association for Cancer Research.
Low, Philip S. et al., "Folate-Mediated Delivery of Therapeutic and Imaging Agents to Cancer Tissue in vivo." British Journal of Pharmacology. vol. 134. Nov. 2001. p. 178P.
Lu, Yinguan; Low, Philip S.; "Folate targeting of haptens to cancer cell surfaces mediates immunotherapy of syngeneic murine tumors," Cancer Immunology Immunotherapy, vol. 51, 2002, 153-162.
Scott et al., "Anti-CD3 Antibody Induces Rapid Expression of Cytokine Genes in Vivo", J. Immunology, 1990. vol. 145(7): 2183-2188.
"Relative Adjuvant Efficacy of Aluminum Hydroxide and Saponin is Related to the Immunogenicity of the antigen." (abstract) Database CAPLUS. Wellcome Res. Lab. R. Bomford. Accession No. 1984:628230.
Kim, Soo Kie et al.; "Effect of immunological adjuvant combinations on the antibody and T-cell response to vaccination with MUCI-KLH and GD3-KLH conjugates". Vaccine: vol. 19. 2001: pp. 530-537: XP.
Behboudi et al., "Isolation and quantification of *Quillaja saponaria* Molina saponins and lipids in iscom-matrix and iscoms,"Vaccine, 13, 1690 (1995).
Hartmann et al., "CpG DNA: a potent signal for growth, activation, and maturation of human dendritic cells." PNAS. 96. 9305-9310 (1999).
Lu Yingjuan and Low, Philip S., "Targeted immunotherapy of cancer: development of antibody-induced cellular immunity." Journal of Pharmacy and Pharmacology. Feb. 2003. vol. 55. No. 2. pp. 163-167.
May, Richard D. et al., "Preclinical Cancer Vaccine Studies in Mice Using a HER-2 Peptide Immunogen Combined with the Saponin-Based Immune Enhancer GPI-0100 and Polysaccharides." FASEB Journal.
Lu et al., "Folate-Mediated Delivery of Macromolecular Anticancer Therapeutic Agents," Advanced Drug Delivery Reviews. vol. 54 (2002). pp. 675-693.
Chu et al., "CpG oligodeoxynucleotides act as adjuvants that switch on T helper 1 (Th1) immunity," J. Exp. Med., 186. 1623-1631 (1997).
Infante-Duarte et al., "Th1/Th2 balance in infection," Springer Semin Immunopathol., 21, 317-338 (1999).
Wang et al., "Design and synthesis of [111In]DTPA-folate for use as a tumor-targeted radiopharmaceutical," Bioconjugate Chemistry. 8. 673-679 (1997).
Sakaguchi et al., "Regulatory T cells and immune tolerance," Cell, 133, 775-787 (2008).
Schwartz, "Natural regulatory T cells and self-tolerance," Nature Immunology, 6, 327-330 (2005).
Harris et al., "Shifts from IgG-2 class to IgG-1 class in CBA and C3H anti-BALB/c antibody," Transplantation. 19. 318-325 (1975) (abstract only).
Azuma et al., "Development of immunoadjuvants for immunotherapy of cancer", *International Immunopharmacology*, 1, pp. 1249-1259 (2001).
Takeuchi et al., "Toll-like receptors; their physiological role and signal transduction system", *International Immunopharmacology*, 1, pp. 625-635 (2001).
Means et al., "Structure and function of Toll-like receptor proteins", *Life Sciences*, 68, pp. 241-258 (2000).
Strominger et al., "Drug-Receptor Interactions: The Example of β-Lactam Antibiotics", *Adv. Pharmacol. Ther. Proc. Int. Congr. Pharmacol.*, 1979, vol. 10, pp. 209-223.
Easty et al., "Up-Regulation of Ephrin-A1 During Melanoma Progression", *Int. J. Cancer* (Pred. Oncol.): 84, pp. 494-501 (1999).
Nakashima-Matsushita et al., "Selective Expression of Folate Receptor β and Its Possible Role in Methotrexate Transport in Synovial Macrophages from Patients with Rheumatoid Arthritis", *Arthritis & Rheumatism*, vol. 42, No. 8, Aug. 1999, pp. 1609-1616.
Brightbill et al., "Host Defense Mechanisms Triggered by Microbial Lipoproteins Through Toll-Like Receptors", *Science*, vol. 285, Jul. 30, 1999, pp. 732-736.
Li et al., "Folate-Mediated Targeting of Antisense Oligodeoxynucleotides to Ovarian Cancer Cells", *Pharmaceutical Research*, vol. 15, No. 10, 1998, pp. 1540-1545.
Citro et al., "Inhibition of leukemia cell proliferation by folic acid-polylysine-mediated introduction of c-myb antisense oligodeoxynucleotides into HL-60 cells", *Br. J. Cancer* (1994), 69, pp. 463-467.
Kensil, "Saponins as Vaccine Adjuvants," *Critical Reviews in Therapeutic Drug Carrier Systems*, 1996; 13:1-55.
Hillman, "Animal Models for Kidney Cancer," in *Tumor Models in Cancer Research*, Beverly A Teicher, ed., Humana Press, 2002, p. 495.

\* cited by examiner

TARGETED CONJUGATES AND RADIATION

CROSS REFERENCE TO RELATED APPLICATIONS

This application is a U.S. national counterpart application of international application serial no. PCT/US2007/002865 filed Feb. 2, 2007, which claims priority under 35 U.S.C. §119(e) to U.S. Provisional Application Ser. No. 60/764,996, filed on Feb. 3, 2006, each incorporated herein by reference.

FIELD OF THE INVENTION

This invention relates to methods and compositions for use in treating disease states mediated by pathogenic cell populations. More particularly, targeted ligand-immunogen conjuates are administered to a diseased host in combination with low dose radiation to enhance the host immune response to the pathogenic cells.

BACKGROUND AND SUMMARY

The mammalian immune system provides a means for the recognition and elimination of tumor cells, other pathogenic cells, and invading foreign pathogens. While the immune system normally provides a strong line of defense, there are still many instances where cancer cells, other pathogenic cells, or infectious agents evade a host immune response and proliferate or persist with concomitant host pathogenicity. The capacity of cancer cells to develop resistance to therapeutic agents, and the adverse side effects of many of the currently available chemotherapeutic agents, particularly in high doses, highlight the need for the development of new therapies with reduced capacity for the development of host resistance and with reduced host toxicity.

Researchers have developed therapeutic protocols for destroying cancer cells by targeting cytotoxic compounds specifically to cancer cells. These protocols utilize toxins conjugated to ligands that bind to receptors unique to or overexpressed by cancer cells in an attempt to minimize delivery of the toxin to normal cells. Another approach for selectively targeting populations of cancer cells or other pathogenic cells in a host is to enhance the host's immune response against the pathogenic cells. One reported strategy for immunotherapy is to bind antibodies, for example, genetically engineered multimeric antibodies, to the tumor cell surface to display the constant region of the antibodies on the cell surface and thereby induce tumor cell killing by various immune system-mediated processes (De Vita, V. T., *Biologic Therapy of Cancer,* 2d ed. Philadelphia, Lippincott, 1995; Soulillou, J. P., U.S. Pat. No. 5,672,486).

Another strategy for relying on host immune competency is the targeting of an anti-T cell receptor antibody or anti-Fc receptor antibody to tumor cell surfaces to promote direct binding of immune cells to tumors (Kranz, D. M., U.S. Pat. No. 5,547,668). A vaccine-based approach has also been described which relies on a vaccine comprising antigens fused to cytokines, with the cytokine modifying the immunogenicity of the vaccine antigen, and, thus, stimulating the immune response to the pathogenic agent (Pillai, S., PCT Publication Number WO 91/11146, published Feb. 7, 1991). Yet another approach for killing unwanted cell populations utilizes IL-2 or Fab fragments of anti-thymocyte globulin linked to antigens to eliminate unwanted T cells (WO 97/37690, published Oct. 16, 1997). There remains a significant need for therapies directed to treatment of disease states characterized by the existence of pathogenic cell populations in an affected host.

The present invention is directed to a method of eliminating cancer cell populations in a host by increasing host immune system recognition of and response to such cell populations. The antigenicity of the cancer cells is increased to enhance the endogenous immune response-mediated elimination of the cancer cells. The method also utilizes the administration of low doses of radiation (e.g., about 0.5 to about 10 Gy per dose) to eliminate the cancer cell populations. The method comprises administration of a ligand-immunogen conjugate wherein the ligand is capable of binding to a population of cancer cells in vivo that uniquely expresses, preferentially expresses, or overexpresses a ligand-binding receptor. The ligand-conjugated immunogen is capable of eliciting antibody production or is capable of being recognized by endogenous or co-administered exogenous antibodies in the host. The immune system-mediated elimination of the cancer cells is directed by the binding of the ligand-conjugated immunogen to a receptor, a transporter, or other surface-presented protein uniquely expressed, overexpressed, or preferentially expressed by the cancer cells. Low doses of radiation (e.g., about 0.5 to about 10 Gy per dose) are administered in combination with the ligand-immunogen conjugates to eliminate the cancer cell populations.

In one illustrative embodiment, a method is provided of enhancing an endogenous immune response-mediated elimination of a population of cancer cells in a host. In one embodiment, the method comprises the steps of administering to the host a composition comprising an immunogen conjugated to a vitamin receptor-binding ligand selected from the group consisting of a vitamin, or an analog or a derivative thereof, and administering to the host a therapeutically effective amount of radiation wherein the amount of radiation ranges from about 0.5 to about 10 Gy per dose.

In another illustrative embodiment, the vitamin is selected from the group consisting of folic acid and other folate receptor-binding ligands. In another embodiment, the immunogen is fluorescein, dinitrophenyl, or an α-galactosyl group. In yet another embodiment, the antibody is exogenous to the host and is co-administered with the conjugate composition. In another embodiment, the method further comprises the step of administering to the host a therapeutic factor such as IL-2, IL-12, IL-15, or combinations thereof, IL-2, IL-12, IL-15, or combinations thereof, in combination with IFN-α or IFN-γ, IL-2, IL-12, IL-15, or combinations thereof, in combination with IFN-α or IFN-γ, or a combination thereof, and GM-CSF. In yet another embodiment, the host has been previously exposed naturally to the immunogen so that the host has a preexisting immunity to the immunogen or the host has been previously exposed to the immunogen by a non-natural process resulting in priming of the host's immune response to the immunogen. In other illustrative embodiments, the endogenous immune response comprises an humoral immune response, a cell-mediated immune response, or an humoral and a cell-mediated immune response.

DETAILED DESCRIPTION OF ILLUSTRATIVE EMBODIMENTS

Figure 1:
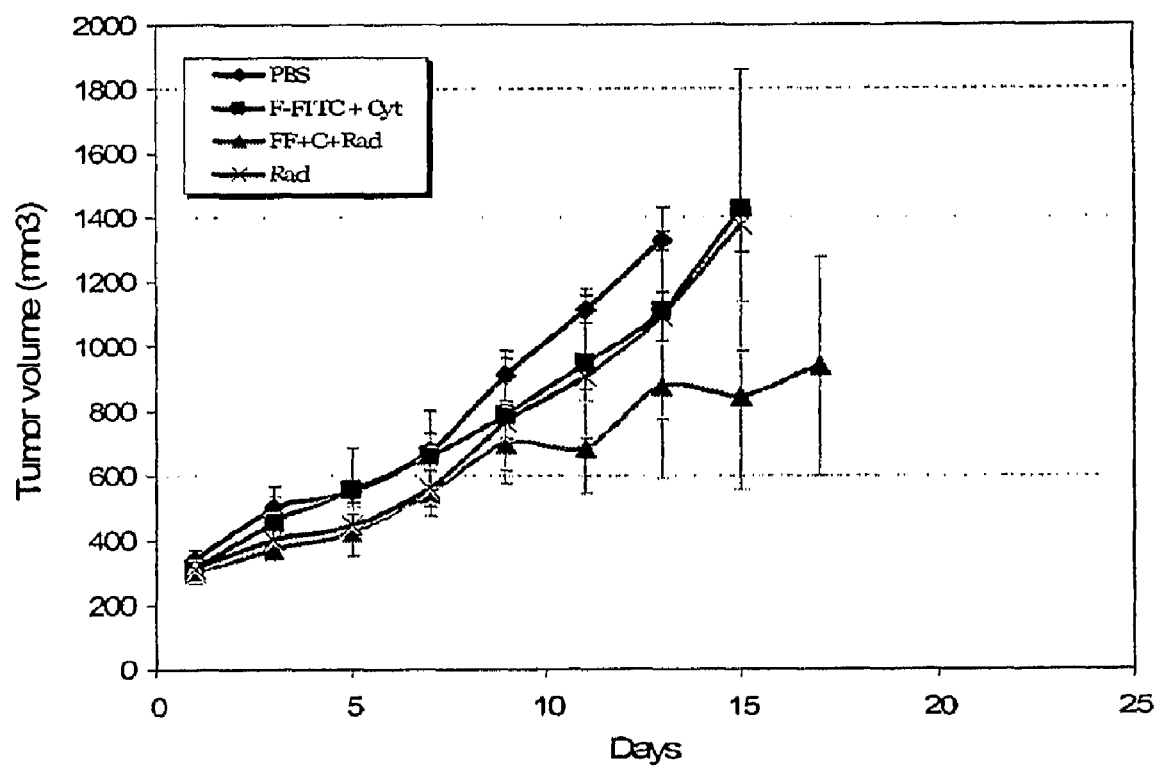
FIG. 1 shows the effect of ligand-immunogen conjugates in combination with radiation on tumor volume. The mice were injected with phosphate-buffered saline (diamonds), folate-FITC, IL-2, and IFN-α (squares), folate-FITC, IL-2, and IFN-α and were treated with radiation (triangles), or were treated with radiation alone (x's).

Methods are provided for the therapeutic treatment of a host with cancer. The methods result in enhancement of the immune response-mediated elimination of pathogenic cell populations by rendering or labeling the pathogenic cells antigenic, utilizing a ligand-immunogen conjugate, resulting in the recognition and elimination of the pathogenic cells by the host immune system. The methods further employ low doses of radiation (e.g., about 0.5 to about 10 Gy per dose) in combination with the ligand-immunogen conjugates to eliminate the pathogenic cells (e.g., cancer cell populations).

In another illustrative embodiment of the invention, in combination with the ligand-immunogen conjugate and radiation, the method can also utilize an additional therapeutic factor, such as a compound capable of stimulating an endogenous immune response, a cell killing agent, a chemotherapeutic agent, a tumor penetration enhancer, a cytotoxic immune cell, and the like to enhance immune response-mediated elimination of the pathogenic cell populations (e.g., cancer cells).

As used herein, the terms "eliminated," "eliminating," and "eliminate," in reference to the disease state, mean reducing the symptoms, completely or partially, of the disease state or preventing the progression, completely or partially, or preventing the reoccurrence of disease, or removing at least some cancer cells.

As used herein, "mediated" means caused by or augmented by. For example, an "immune response-mediated" effect means that the immune response can directly cause the effect or can augment the effect.

As used herein "distal to the site of radiation" in reference to tumors or cancer cells means a tumor or cancer cells that are not irradiated or are not part of the tumor that is irradiated.

The method of the present invention is utilized to enhance an endogenous immune response-mediated elimination of a population of pathogenic cells in a host harboring the population of pathogenic cells (e.g., cancer cells). The invention is applicable to populations of pathogenic cells that cause a variety of pathologies, such as cancer. In one illustrative embodiment, the population of pathogenic cells can be a cancer cell population that is tumorigenic, including benign tumors and malignant tumors, or a cancer cell population that non-tumorigenic. In another illustrative embodiment, the cancer cell population can arise spontaneously or by such processes as mutations present in the germline of the host or somatic mutations, or the cancer may be chemically, virally, or radiation-induced. In another embodiment, the invention can be used to treat such cancers as carcinomas, sarcomas, lymphomas, Hodgekin's disease, melanomas, mesotheliomas, Burkitt's lymphoma, nasopharyngeal carcinomas, leukemias, and myelomas. In yet another embodiment, the cancer cell population can include, but is not limited to, oral, thyroid, endocrine, skin, gastric, esophageal, laryngeal, pancreatic, colon, bladder, bone, ovarian, cervical, uterine, breast, testicular, prostate, rectal, kidney, liver, and lung cancers.

The methods described herein can be used for both human clinical medicine and veterinary applications. Thus, in one embodiment, the host harboring the population of pathogenic cells and treated with the ligand-immunogen conjugates in combination with low dose irradiation can be a human or, in another embodiment, in the case of veterinary applications, can be a laboratory, agricultural, domestic, or wild animal. In various embodiments, the methods described herein can be applied to hosts including, but not limited to, humans, laboratory animals such rodents (e.g., mice, rats, hamsters, etc.), rabbits, monkeys, chimpanzees, domestic animals such as dogs, cats, and rabbits, agricultural animals such as cows, horses, pigs, sheep, goats, and wild animals in captivity such as bears, pandas, lions, tigers, leopards, elephants, zebras, giraffes, gorillas, dolphins, and whales.

In one illustrative embodiment, the ligand-immunogen conjugate is administered to the host parenterally, e.g., intradermally, subcutaneously, intramuscularly, intraperitoneally, or intravenously. In other illustrative embodiments, the conjugate can be administered to the host using by other medically useful processes, and any effective dose and suitable therapeutic dosage form, including prolonged release dosage forms, can be used. In other embodiments, the method of the present invention utilizing the administration of ligand-immunogen conjugates in combination with low dose irradiation can be used in combination with surgical removal of a tumor, chemotherapy, or biological therapies such as other immunotherapies including, but not limited to, monoclonal antibody therapy, treatment with immunomodulatory agents, adoptive transfer of immune effector cells, treatment with hematopoietic growth factors, cytokines, and vaccination.

In accordance with the methods described herein, the ligand-immunogen conjugates can be selected from a variety of ligands and immunogens. In one embodiment, the ligands are capable of specifically eliminating a population of pathogenic cells (e.g., cancer cells) in the host due to preferential expression of a receptor for the ligand, accessible for ligand binding, on the pathogenic cells. In one illustrative embodiment, the ligand can be a vitamin. In various embodiments, the vitamins that can be used include folic acid, analogs and derivatives of folic acid and other folate receptor-binding molecules, and other vitamins, including niacin, pantothenic acid, riboflavin, thiamine, biotin, vitamin $B_{12}$, vitamins A, D, E and K, other related vitamin receptor-binding molecules, analogs and derivatives thereof, and combinations thereof.

In one embodiment, the ligand can be folic acid, a folic acid analog, or another folate receptor-binding molecule. Analogs of folate that can be used include folinic acid, pteropolyglutamic acid, and folate receptor-binding pteridines such as tetrahydropterins, dihydrofolates, tetrahydrofolates, and their deaza and dideaza analogs. The terms "deaza" and "dideaza"

analogs refers to the art recognized analogs having a carbon atom substituted for one or two nitrogen atoms in the naturally occurring folic acid structure. For example, the deaza analogs include the 1-deaza, 3-deaza, 5-deaza, 8-deaza, and 10-deaza analogs. The dideaza analogs include, for example, 1,5 dideaza, 5,10-dideaza, 8,10-dideaza, and 5,8-dideaza analogs. The foregoing folic acid analogs are conventionally termed "folates," reflecting their capacity to bind to folate receptors. Other folate receptor-binding analogs include aminopterin, amethopterin (methotrexate), $N^{10}$-methylfolate, 2-deamino-hydroxyfolate, deaza analogs such as 1-deazamethopterin or 3-deazamethopterin, and 3',5'-dichloro4-amino-4-deoxy-$N^{10}$-methylpteroylglutamic acid (dichloromethotrexate).

In other illustrative embodiments, other ligands that can be used include peptide ligands identified from library screens, tumor-specific peptides, tumor-specific aptamers, tumor-specific carbohydrates, tumor-specific monoclonal or polyclonal antibodies, Fab or scFv (i.e., a single chain variable region) fragments of antibodies such as, for example, an Fab fragment of an antibody directed to EphA2 or other proteins specifically expressed or uniquely accessible on metastatic cancer cells, small organic molecules derived from combinatorial libraries, growth factors, such as EGF, FGF, insulin, and insulin-like growth factors, and homologous polypeptides, somatostatin and its analogs, transferrin, lipoprotein complexes, bile salts, selectins, steroid hormones, Arg-Gly-Asp containing peptides, retinoids, various Galectins, δ-opioid receptor ligands, cholecystokinin A receptor ligands, ligands specific for angiotensin AT1 or AT2 receptors, peroxisome proliferator-activated receptor γ ligands, β-lactam antibiotics, small organic molecules, and other molecules that bind specifically to a receptor preferentially expressed, overexpressed, or uniquely expressed on the surface of cancer or other pathogenic cells, or fragments of any of these molecules. It is also contemplated, in another illustrative embodiment, that ligands binding to any tumor antigens or other molecules preferentially expressed, overexpressed, or uniquely expressed on the surface of tumor cells can be used.

The binding site for the ligand may include receptors for any molecule capable of specifically binding to a receptor wherein the receptor or other protein is preferentially expressed on the population of pathogenic cells, including, for example, receptors for growth factors, vitamins, peptides, including opioid peptides, hormones, antibodies, carbohydrates, and small organic molecules. In another embodiment, it is contemplated that tumor-specific antigens may function as binding sites for ligands in the methods described herein. An illustrative example of a tumor-specific antigen that could function as a binding site for ligand-immunogen conjugates is an extracellular epitope of a member of the Ephrin family of proteins, such as EphA2. EphA2 expression is restricted to cell-cell junctions in normal cells, but EphA2 is distributed over the entire cell surface in metastatic tumor cells. Thus, EphA2 on metastatic cancer cells would be accessible for binding to, for example, an Fab fragment of an antibody conjugated to an immunogen, whereas the protein would not be accessible for binding to the Fab fragment on normal cells, resulting in a ligand-immunogen conjugate specific for metastatic cancer cells. In another embodiment, combinations of ligand-immunogen conjugates can be used to maximize targeting of the pathogenic cells for elimination by an acquired or innate immune response or by co-administered antibodies. This embodiment is used in accordance with the method described herein in combination with low dose radiation.

Illustrative immunogens for use in the present invention are immunogens that are capable of eliciting antibody production in a host or that have previously elicited antibody production in a host resulting in a preexisting immunity or that constitute part of the innate immune system. In another illustrative embodiment, antibodies directed against the immunogen can be administered to the host to establish a passive immunity. In illustrative embodiments, immunogens for use in the invention include antigens or antigenic peptides against which a preexisting immunity has developed via normally scheduled vaccinations or prior natural exposure to such agents as poliovirus, tetanus, typhus, rubella, measles, mumps, pertussis, tuberculosis, and influenza antigens. In such cases, the ligand-immunogen conjugates will be used to redirect a previously acquired humoral or cellular immunity to a population of pathogenic cells (e.g., cancer cells) in the host for elimination of the pathogenic cells.

In other illustrative embodiments, immunogens that can be used include antigens or antigenic peptides to which the host has developed a novel immunity through immunization against an unnatural antigen or hapten (e.g., fluorescein or dinitrophenyl) and antigens against which an innate immunity exists (e.g., super antigens, such as α-galactosyl groups, and muramyl dipeptide).

The ligands and immunogens of the invention can be conjugated by utilizing any art-recognized method of forming a conjugate. In illustrative embodiments, this can include covalent, ionic, or hydrogen bonding of the ligand to the immunogen, either directly or indirectly via a linking group such as a divalent linker. In various embodiments, the conjugate is formed by covalent bonding of the ligand to the immunogen through the formation of amide, ester or imino bonds between acid, aldehyde, hydroxy, amino, or hydrazo groups on the respective components of the conjugate (i.e., ligand and immunogen). In one embodiment of the invention, the ligand is folic acid, an analog of folic acid, or any other folate-receptor binding molecule, and the folate ligand is conjugated to the immunogen by a procedure that utilizes trifluoroacetic anhydride to prepare γ-esters of folic acid via a pteroyl azide intermediate. In an illustrative embodiment, this procedure can result in the synthesis of a folate ligand, conjugated to the immunogen only through the γ-carboxy group of the glutamic acid groups of folate wherein the γ-conjugate binds to the folate receptor with high affinity, avoiding the formation of mixtures of an α-conjugate and the γ-conjugate. In another embodiment, pure α-conjugates can be prepared from intermediates wherein the γ-carboxy group is selectively blocked, the α-conjugate is formed and the γ-carboxy group is subsequently deblocked using art-recognized organic synthesis protocols and procedures.

In various embodiments, vitamin-immunogen conjugates can be formed with biotin and riboflavin as well as folate. Procedures for conjugating vitamins to immunogens can be found in U.S. Pat. Nos. 5,108,921, 5,416,016, and 5,635,382, each incorporated herein by reference, and in U.S. Patent Application Publication No. US2005-0002942-A1 and U.S. Patent Application Ser. No. 60/590,580, each incorporated herein by reference.

The ligand-immunogen conjugates of the invention enhance an endogenous immune response-mediated elimination of a population of pathogenic cells (e.g., cancer cells). In illustrative embodiments, the endogenous immune response can include an humoral immune response, a cell-mediated immune response, and any other immune response endogenous to the host, including complement-mediated cell lysis, antibody-dependent cell-mediated cytoxicity (ADCC), antibody opsonization leading to phagocytosis, clustering of receptors upon antibody binding resulting in signaling of apoptosis, antiproliferation, or differentiation, and direct immune cell recognition of the delivered antigen or hapten. In another embodiment, the endogenous immune response can employ the secretion of cytokines that regulate such processes as the multiplication and migration of immune cells. In illustrative embodiments, the endogenous immune response can include the participation of such immune cell types as B cells, T cells, including helper and cytotoxic T cells, macrophages, natural killer cells, neutrophils, LAK cells, and the like.

In illustrative embodiments, the humoral response can be a response induced by such processes as normally scheduled vaccination, or active immunization with a natural antigen or an unnatural antigen or hapten (e.g., fluorescein or dinitrophenyl), with the unnatural antigen inducing a novel immunity. In one embodiment, active immunization can involve multiple injections of the unnatural antigen or hapten scheduled outside of a normal vaccination regimen to induce the novel immunity.

In one embodiment, the humoral response can result from an innate immunity where the host animal has a natural preexisting immunity, such as an immunity to α-galactosyl groups. In another embodiment, a passive immunity can be established by administering antibodies to the host such as natural antibodies collected from serum or monoclonal antibodies that may or may not be genetically engineered antibodies, such as humanized antibodies. The utilization of a particular amount of an antibody reagent to develop a passive immunity, and the use of a ligand-immunogen conjugate where the passively administered antibodies are directed to the immunogen, provides the advantage of a standard set of reagents to be used in cases where a patient's preexisting antibody titer is not therapeutically useful. In one embodiment, the passively administered antibodies can be "co-administered" with the ligand-immunogen conjugate. "Co-administration" is defined as administration of antibodies at a time prior to, at the same time as, or at a time following administration of the ligand-immunogen conjugate.

In one embodiment where active immunization is used, the host can be preimmunized with a hapten-carrier (e.g., KLH or BSA) conjugate, for example, to elicit a preexisting immunity to the hapten. In this embodiment, the ligand-immunogen (e.g., hapten) conjugate can then be administered to the host resulting in an humoral or cell-mediated immune response, or both, directed against the ligand-hapten conjugate bound to the targeted pathogenic cells. Illustrative carriers that can be used in accordance with the invention include keyhole limpet hemocyanin (KLH), haliotis tuberculata hemocyanin (HtH), inactivated diptheria toxin, inactivated tetanus toxoid, purified protein derivative (PPD) of *Mycobacterium tuberculosis*, bovine serum albumin (BSA), ovalbumin (OVA), g-globulins, thyroglobulin, peptide antigens, and synthetic carriers, such as poly-L-lysine, dendrimer, and liposomes. In various embodiments, effective doses of the hapten-carrier conjugate can range from about 1 μg to about 100 mg per host, or from about 10 μg to about 50 mg per host, or from about 50 μg to about 10 mg per host.

Illustratively, adjuvants can be administered during the preimmunization and such adjuvants include saponin adjuvants (e.g., the quillajasaponins), CpG, 3-deacylated monophosphoryl lipid A (MPL), Bovine Calmette-Guerin (BCG), double stem-loop immunomodulating oligodeoxyribonucleotides (d-SLIM), heat-killed *Brucella abortus* (HKBA), heat-killed *Micobacterium vaccae* (SRL172), inactivated vaccinia virus, cyclophosphamide, prolactin, thalidomide, actimid, revimid, and the like. Saponin adjuvants and methods of their preparation and use are described in detail in U.S. Pat. Nos. 5,057,540; 5,273,965; 5,443,829; 5,508,310; 5,583,112; 5,650,398; 5,977,081; 6,080,725; 6,231,859; and 6,262,029 incorporated herein by reference. In various embodiments, effective doses of the adjuvant can range from about 0.01 μg to about 100 mg per host, or from about 100 μg to about 50 mg per host, or from about 500 μg to about 10 mg per host.

In one embodiment, the preexisting antibodies, induced antibodies, or passively administered antibodies can be redirected to the pathogenic cells (e.g., cancer cells) by preferential binding of the ligand-immunogen conjugates to these cells and the pathogenic cells can be killed by complement-mediated lysis, ADCC, antibody-dependent phagocytosis, or antibody clustering of receptors. In other embodiments, the cytotoxic process can also involve other types of immune responses, such as cell-mediated immunity, as well as secondary responses that arise when the attracted antigen-presenting cells phagocytose the unwanted cells and present natural tumor antigens, for example, to the immune system for elimination of the cells bearing the antigens.

In one embodiment, an additional composition comprising a therapeutic factor can be administered to the host in combination with the ligand-immunogen conjugate and radiation to enhance the endogenous immune response-mediated elimination of the population of pathogenic cells, or more than one additional therapeutic factor can be administered. Illustratively, the therapeutic factor can be selected from a compound capable of stimulating an endogenous immune response, a chemotherapeutic agent, or another therapeutic factor capable of complementing the efficacy of the administered ligand-immunogen conjugate and radiation.

Illustratively, compounds or compositions capable of stimulating an endogenous immune response include, but are not limited to, cytokines or immune cell growth factors such as interleukins 1-18, stem cell factor, basic FGF, EGF, G-CSF, GM-CSF, FLK-2 ligand, HILDA, MIP-1α, TGF-α, TGF-β, M-CSF, IFN-α, IFN-β, IFN-γ, soluble CD23, LIF, and combinations thereof.

In one embodiment, therapeutically effective combinations of these cytokines can be used. In one embodiment, therapeutically effective amounts of IL-2, for example, in amounts ranging from about 5000 IU/dose/day to about 500,000 IU/dose/day in a multiple dose daily regimen, and IFN-α, for example, in amounts ranging from about 7500 IU/dose/day to about 150,000 IU/dose/day in a multiple dose daily regimen, can be used along with folate-fluorescein conjugates and radiation to eliminate pathogenic cells (e.g., cancer cells) in a host harboring such a population of cells. In another embodiment, therapeutically effective amounts of IL-2, for example, in amounts ranging from about 0.1 MIU/m$^2$/dose/day to about 60 MIU/m$^2$/dose/day in a multiple dose daily regimen, and IFN-α, for example, in amounts ranging from about 0.1 MIU/m$^2$/dose/day to about 10 MIU/m$^2$/dose/day in a multiple dose daily regimen, can be used (MIU=million international units; m$^2$=approximate body surface area of an average human). In another illustrative embodiment, IL-12 and IFN-α can be used in therapeutically effective amounts, and in yet another illustrative embodiment IL-15 and IFN-α can be used in therapeutically effective amounts. In an alternate illustrative embodiment IL-2, IFN-α, or IFN-γ, and GM-CSF can be used in combination.

In another embodiment, the therapeutic factor(s) used, such as IL-2, IL-12, IL-15, IFN-α, IFN-γ, and GM-CSF, including combinations thereof, activate(s) natural killer cells and/or T cells. In another embodiment, the therapeutic factor or combinations thereof, including an interleukin in combination with an interferon and GM-CSF, can activate other immune effector cells such as macrophages, B cells, neutrophils, LAK cells, or the like. Illustratively, other effective combinations of cytokines including combinations of other interleukins and interferons and colony stimulating factors can be used.

Illustratively, the additional therapeutic factor can be a chemotherapeutic agent, including adrenocorticoids, alkylating agents, antiandrogens, antiestrogens, androgens, estrogens, antimetabolites such as cytosine arabinoside, purine analogs, pyrimidine analogs, and methotrexate, busulfan, carboplatin, chlorambucil, cisplatin and other platinum compounds, tamoxiphen, taxol, cyclophosphamide, plant alkaloids, prednisone, hydroxyurea, teniposide, antibiotics such as mitomycin C and bleomycin, nitrogen mustards, nitrosureas, vincristine, vinblastine, colchicine, inflammatory and proinflammatory agents, and any other art-recognized chemotherapeutic agent.

In one embodiment, the elimination of the population of pathogenic cells (e.g., cancer cells) can comprise a reduction or elimination of tumor mass resulting in a therapeutic response. In one embodiment, in the case of a tumor, the elimination may be an elimination of cells of the primary tumor or of cells that have metastasized or are in the process of dissociating from the primary tumor. In another embodiment, a prophylactic treatment to prevent return of a tumor after its elimination by the method described herein using any therapeutic approach including the method described herein, surgical removal of the tumor, chemotherapy, or biological therapy can also be used. In one illustrative embodiment, the prophylactic treatment can be an initial treatment with the ligand-immunogen conjugate, such as treatment in a multiple dose daily regimen, and/or may be an additional treatment or series of treatments after an interval of days or months following the initial treatments(s).

In yet another embodiment, pharmaceutical compositions are provided comprising an amount of a ligand-immunogen conjugate effective to "label" a population of pathogenic cells in a host for elimination by an endogenous immune response or by co-administered antibodies in accordance with the method described herein (i.e., a therapeutically effective amount in accordance with the method described herein). In an illustrative embodiment, the pharmaceutical composition can further comprise a therapeutically effective amount (in accordance with the method described herein) of an additional therapeutic factor selected from the group consisting of a cell killing agent, a tumor penetration enhancer, a chemotherapeutic agent, a cytotoxic immune cell, and a compound capable of stimulating an endogenous immune response. Illustratively, the therapeutic factor can be a cytokine such as IL-2, IL-12, or IL-15, or combinations of cytokines, including IL-2, IL-12, or IL-15 and interferons such as IFN-α or IFN-γ or can include combinations of interferons, interleukins, and colony stimulating factors, such as GM-CSF.

The unitary daily dosage of the ligand-immunogen conjugate can vary significantly depending on the host condition, the disease state being treated, the molecular weight of the conjugate, its route of administration and tissue distribution, and the possibility of co-usage of other therapeutic treatments. The amount to be administered to a host is based on body surface area, weight, and physician assessment of host condition. In various embodiments, an effective dose can range from about 1 ng/kg to about 1 mg/kg, from about 1 µg/kg to about 500 µg/kg, from about 1 ng/kg to about 10 µg/kg, or from about 1 ng/kg to about 1 µg/kg.

Any effective regimen for administering the ligand-immunogen conjugate, the therapeutic factor, or radiation can be used. In illustrative embodiments, the ligand-immunogen conjugate and therapeutic factor can be administered as single doses, or they can be divided and administered as a multiple-dose daily regimen. In other embodiments, a staggered regimen, for example, one to three days per week, or for five consecutive days with two days off, can be used as an alternative to daily treatment, and for the purpose of defining this invention such intermittent or staggered daily regimen is considered to be equivalent to every day treatment and within the scope of this invention. In one embodiment, the host is treated with multiple injections of the ligand-immunogen conjugate and the therapeutic factor to eliminate the population of pathogenic cells (e.g., cancer cells). In another embodiment, the host is injected multiple times (typically about 2 to about 50 times or about 5 to about 20 times) with the ligand-immunogen conjugate, for example, at 12-72 hour intervals or at 48-72 hour intervals or at 24 hour intervals. In yet another embodiment, additional injections of the ligand-immunogen conjugate can be administered to the host at an interval of days or months after the initial injections(s) and the additional injections can prevent or slow recurrence of disease. In another embodiment, the initial injection(s) of the ligand-immunogen conjugate can prevent recurrence of disease.

In various embodiments, the therapeutic factor can be administered to the host prior to, after, or at the same time as the ligand-immunogen conjugate and the therapeutic factor can be administered as part of the same composition containing the conjugate or as part of a different composition than the ligand-immunogen conjugate. Any such therapeutic composition containing the therapeutic factor at a therapeutically effective dose can be used in the present invention. In other embodiments, more than one type of ligand-immunogen conjugate can be used. For example, the host can be preimmunized with both fluorescein and dinitrophenyl and subsequently treated in a co-dosing protocol with fluorescein and dinitrophenyl conjugated to the same or different ligands.

In one embodiment, the ligand-immunogen conjugate and the therapeutic factor can be injected parenterally and such injections can be intraperitoneal injections, subcutaneous injections, intramuscular injections, intravenous injections or intrathecal injections. In another embodiment, the ligand-immunogen conjugate and/or the therapeutic factor can be delivered using a slow pump. Examples of parenteral dosage forms include aqueous solutions of the active agent, in an isotonic saline, 5% glucose or other well-known pharmaceutically acceptable liquid carriers such as liquid alcohols, glycols, esters, and amides. In one embodiment, the parenteral dosage form in accordance with this invention can be in the form of a reconstitutable lyophilizate. Illustratively, any of a number of prolonged release dosage forms known in the art can be administered such as, for example, the biodegradable carbohydrate matrices described in U.S. Pat. Nos. 4,713,249; 5,266,333; and 5,417,982, the disclosures of which are incorporated herein by reference.

In various embodiments, the radiation dose can range from about 0.5 to about 10 Gy per dose, about 0.5 to about 8 Gy per dose, about 0.5 to about 6 Gy per dose, about 0.5 to about 5 Gy per dose, about 0.5 to about 4 Gy per dose, about 0.5 to about 3 Gy per dose, about 0.5 to about 2 Gy per dose, about 1 to about 10 Gy per dose, about 1 to about 8 Gy per dose, about 1 to about 6 Gy per dose, about 1 to about 5 Gy per dose, about 1 to about 4 Gy per dose, or about 1 to about 3 Gy per dose.

The radiation can be administered by any method known in the art and using any device known in the art and calibrated to give the desired radiation dose to the host. The radiation can also be administered according to any effective regimen. Illustratively, the radiation dose can be administered once per week, twice per week, three times per week, four times per week, or five times per week, for as many weeks as is therapeutically effective. In another illustrative embodiment, the radiation dose can be administered one time. In another illustrative embodiment, the radiation dose can be administered on consecutive days. In yet another illustrative embodiment, an intermittent daily regimen can be used (e.g., with one, two, three, four, five, six, seven days, etc. between doses). The radiation can be administered as many times as is desired to give a therapeutic effect.

Any of the above-described compositions can be in the form of a kit containing any combination of the above-described compositions for use in the method described herein.

for 45 minutes with nitrogen bubbling. The product was collected by lyophilization. Purification was carried out using preparative HPLC (Rigel).

EXAMPLE 2

Synthesis of Folate Fluorescein

Folate-FITC was synthesized as described by Kennedy, M. D. et al. in *Pharmaceutical Research*, Vol. 20(5); 2003.

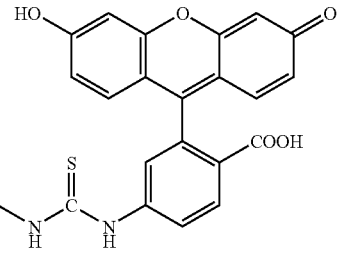

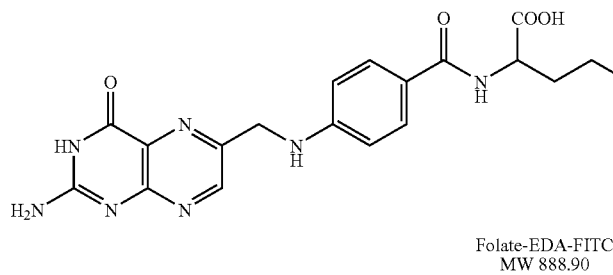

Folate-EDA-FITC
MW 888.90

In one embodiment, the compositions that can be included in the kit are selected from the group consisting of an adjuvant, a hapten-carrier conjugate, a ligand-immunogen conjugate, and a therapeutic factor. In this embodiment, the kits can also include instructions for use of these compositions in combination with radiation in accordance with the method described herein.

EXAMPLE 1

Solid Phase Synthesis of Folate Conjugate

The precursor of folate, $N^{10}$-TFA-Pteroic acid was synthesized according to standard procedures. Fmoc-Lys(Mtt)-Wang resin was soaked in DMF for 20 minutes with nitrogen bubbling before the reaction. 20% piperidine was added to cleave the Fmoc protective group. 2.5 e.q. Fmoc-Glu-OtBu, HOBT and HBTU, dissolved in DMF, as well as 4 e.q. DIPEA were added to the reaction funnel. After 2 hours of nitrogen bubbling at room temperature, the Fmoc cleavage step was repeated with 20% piperidine. 1.5 e.q. $N^{10}$-TFA-Pteroic acid and 2.5 e.q. HOBT and HBTU, dissolved in 1:1 DMF/DMSO (dimethylformamide/dimethylsulfoxide), as well as 4 e.q. DIPEA were then added to the reaction for 4 hours with bubbling with nitrogen. The product was then washed with DMF, DCM (dichloromethane), methanol and isopropyl alcohol thoroughly and dried under nitrogen. 1% TFA/DCM (trifluoroacetic acid/dichloromethane) was used to cleave the Mtt (Mtt=4-methyl-trityl) group. 2.5 e.q. FITC, dissolved in DMF, and 4 e.q. DIPEA were added to the resin and reaction was carried out at room temperature overnight under reduced light conditions. Cleavage of the conjugates was achieved by TFA:TIPS:H$_2$O (95:2.5:2.5). The crude product was collected by precipitation with cool ether. The crude product was lyophilized overnight. On the second day, the crude product was hydrolyzed using 10% ammonium hydroxide (pH=10)

EXAMPLE 3

Effect of Ligand-Immunogen Conjugates in Combination with Radiation on Tumor Volume Six to eight-week old (~20-22 grams) female Balb/c mice were immunized subcutaneously at multiple sites with fluorescein (FITC)-labeled keyhole limpet hemocyanin (KLH) and were injected with GPI-0100, a saponin adjuvant. After assuring that anti-FITC antibody titers were high in all mice (as evidenced by the results of ELISA assays of serum samples of the mice), each animal was injected subcutaneously in the shoulder with 1×10$^6$ M109 cells following the pre-immunization with FITC-KLH. M109 cells are a syngeneic lung cancer cell line that expresses high levels of the folate receptor. Cancer loci were then allowed to attach and grow. When the tumor size reached about 300 mm$^2$ (about 2 weeks post M109 cell injection), treatments were initiated (day 1).

The mice were divided into four groups (4 mice per group). One group was injected subcutaneously with phosphate-buffered saline (PBS). Two other groups were injected subcutaneously with 500 nmoles/kg of folate-FITC and 20,000 IU/dose of recombinant human IL-2 in a series of 5 daily injections for three weeks (5 days on and 2 days off). The mice were also injected subcutaneously with IFN-α at 25,000 IU/dose (3 times per week for 3 weeks). One of these groups also received a single dose of radiation of 3 Gy on day 1. The fourth group received only a single dose of radiation of 3 Gy on day 1. The radiation was performed with a device approved for human use and calibrated to give the desired radiation dose to mice. The electron beam generated by the device had a one centimeter diameter and a penetration depth of about one centimeter assuring that only the tumor and not the normal tissue was irradiated.

The efficacy of these therapies were then evaluated by monitoring tumor volumes. Tumor volumes were calculated using the equation $V=a \times b^2/2$, where "a" is the length of the tumor and "b" is the width expressed in millimeters. The tumors were measured using calipers. As shown in FIG. 1, folate-FITC and cytokines act synergistically with low dose radiation to eliminate tumors in mice.

EXAMPLE 4

Figure 2:
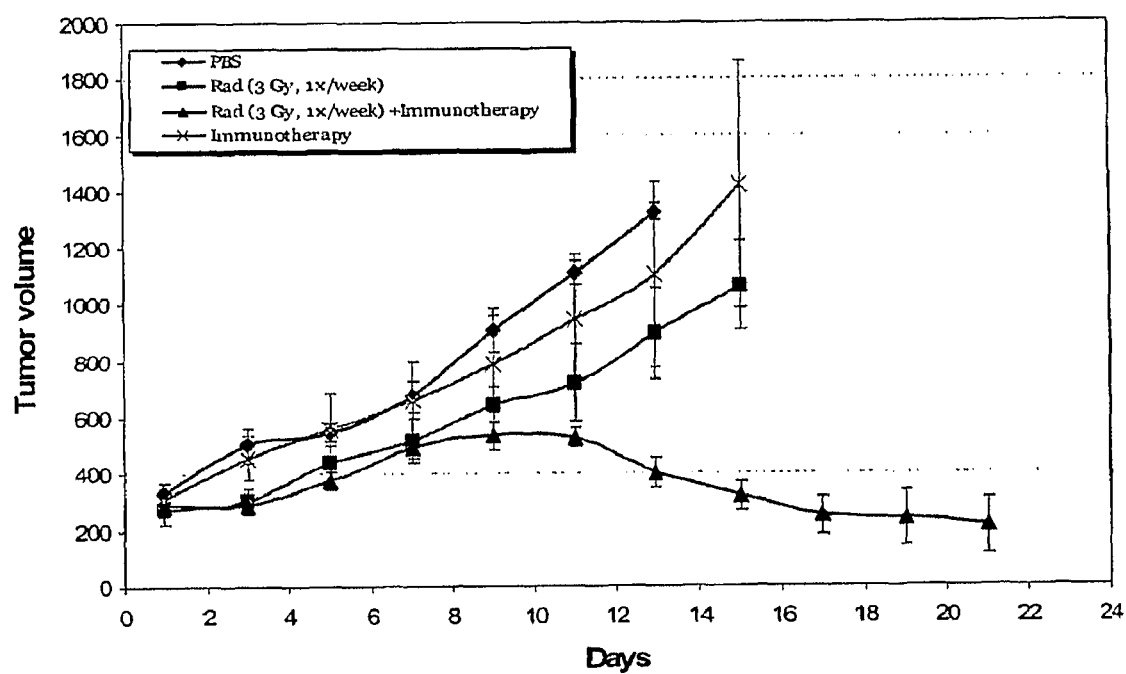
FIG. 2 shows the effect of ligand-immunogen conjugates in combination with radiation on tumor volume. The mice were injected with phosphate-buffered saline (diamonds), folate-FITC, IL-2, and IFN-α (x's), folate-FITC, IL-2, and IFN-α and were treated with radiation (triangles), or were treated with radiation alone (squares).

Effect of Ligand-Immunogen Conjugates in Combination with Radiation on Tumor Volume The procedures were similar to those described in Example 3 except that the radiation was given in three doses of three Gy each on days 1, 5, and 12. As shown in FIG. 2, folate-FITC plus IL-2 and IFN-α(i.e., denoted as folate immunotherapy or immunotherapy below) are synergistic with low dose radiation to eliminate tumors in mice. Two out of the four mice in this treatment group were tumor-free at the end of the assay.

EXAMPLE 5

Effect on Non-Irradiated Tumors

Figure 3:
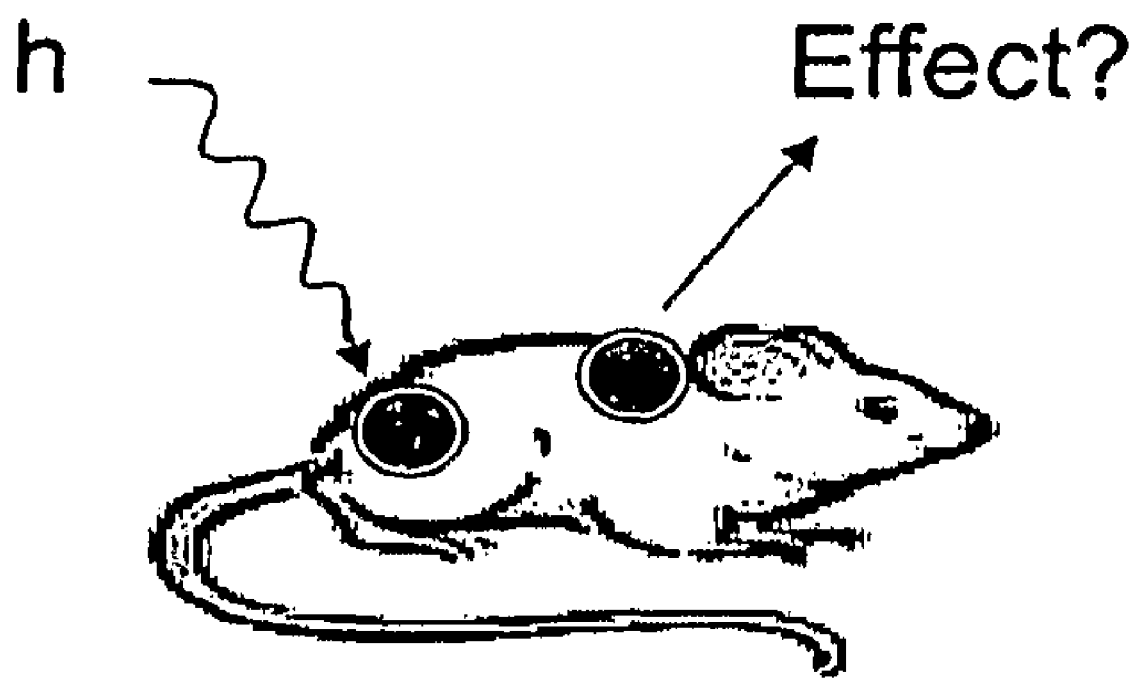
FIG. 3 shows a diagram of radiation treatment of mice injected at two sites with M109 cells.

The procedures were similar to those described in Example 3 except that the mice (6 mice per group) were injected with M109 cells at the base of the neck and at the base of the tail (see FIG. 3). The treatment started when the tumor at the base of the neck reached 300 mm². The tumor at the base of the tail was irradiated at days 1 and 5 with 3 Gy per dose. The tumor at the base of the neck was not irradiated.

Figure 4:
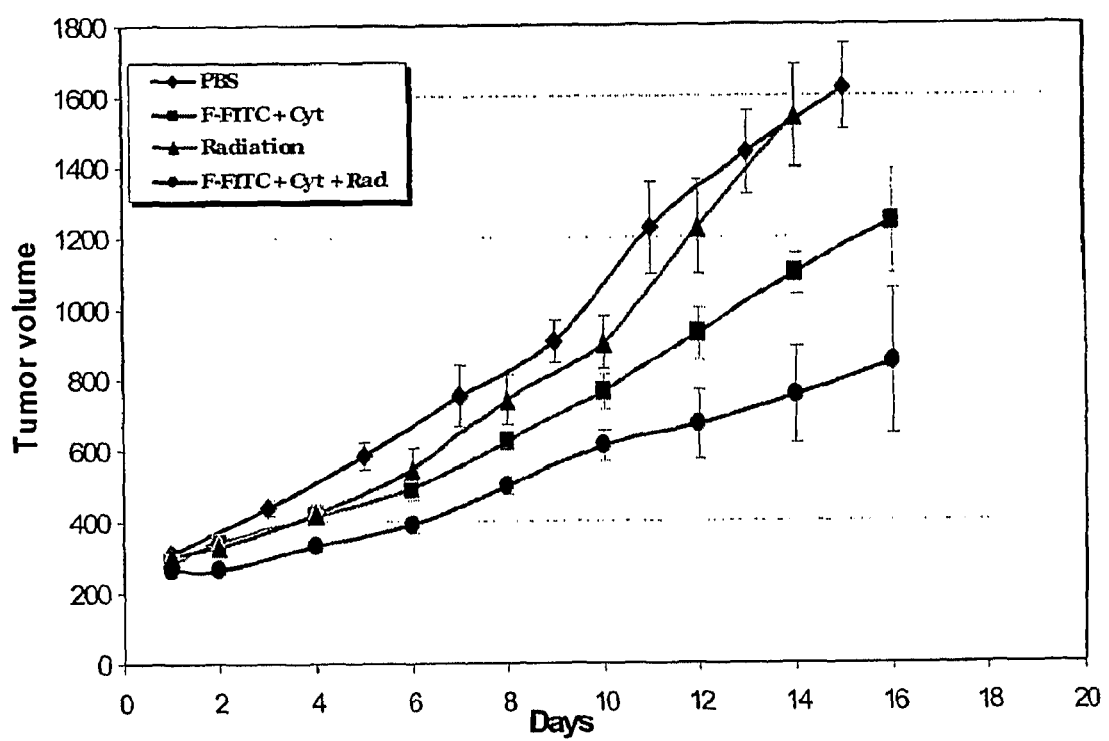
FIG. 4 shows the effect of ligand-immunogen conjugates in combination with radiation on tumor volume for a non-irradiated tumor. The mice were injected with phosphate-buffered saline (diamonds), folate-FITC, IL-2, and IFN-α (squares), folate-FITC, IL-2, and IFN-α and were treated with radiation (circles), or were treated with radiation alone (triangles).

As shown in FIG. 4, the combination of folate-FITC, cytokines, and radiation yields an improved response for tumors on the same animal that were not irradiated. These results indicate that this combination therapy generates a systemic and synergistic antitumor response that can even suppress tumor growth of nonirradiated tumors. Two out of six mice treated with this combination therapy were completely tumor-free after this treatment. The data show that this combination therapy is beneficial in the treatment of metastatic folate receptor-positive tumors.

EXAMPLE 6

Effect of Ligand-Immunogen Conjugates in Combination with Taxol

Figure 5:
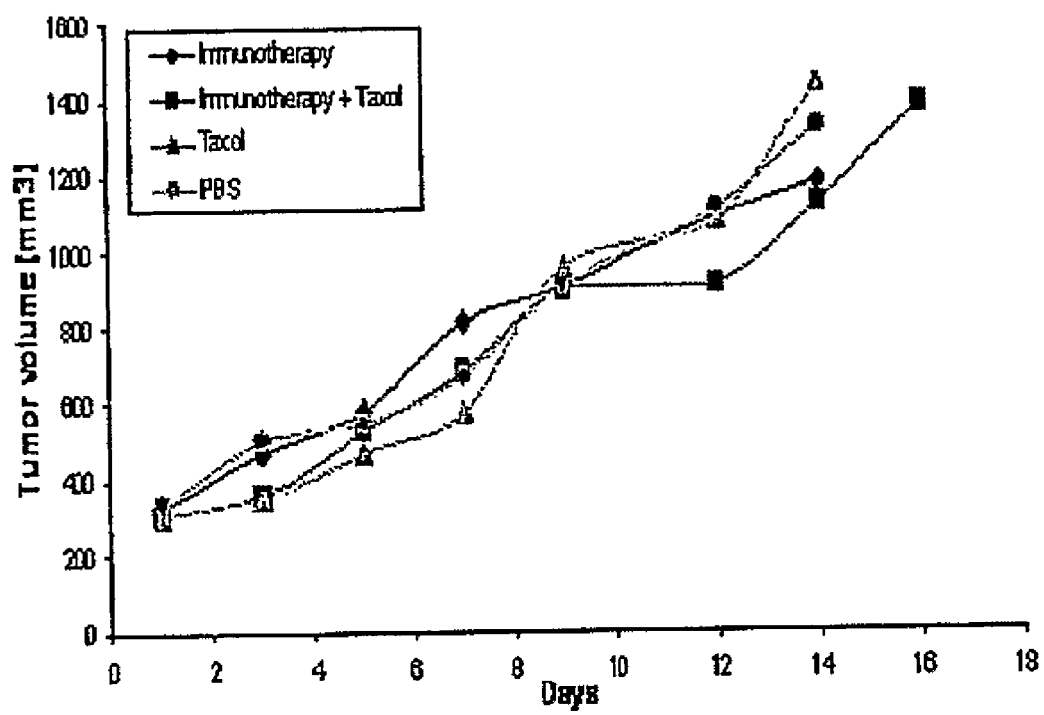
FIG. 5 shows the effect of ligand-immunogen conjugates in combination with taxol on tumor volume. The mice were injected with phosphate-buffered saline (circles), folate-FITC, IL-2, and IFN-α (diamonds), folate-FITC, IL-2, and IFN-α and were treated with taxol (squares), or were treated with taxol (triangles).

The procedures were similar to those described in Example 3 except that the mice were treated with 3 doses of taxol (20 mg/kg, every other day) in place of radiation. As shown in FIG. 5, folate-FITC and cytokines were not synergistic with taxol to eliminate the tumor mass in mice implanted with M109 tumors, indicating that the synergistic effect observed with the use of radiation in combination with the method described herein does not occur with a known therapy (i.e., taxol treatment) commonly used in combination therapies.

EXAMPLE 7

Flow Cytometric Analysis of Tumor-Infiltrating Immune Cells

Mice bearing M109 tumors, one on the dorsal median area and the other at the base of the neck, were divided into four groups and treated as follows: (a) no treatment, (b) radiation alone, (c) folate immunotherapy, and (d) radiation plus folate immunotherapy. The folate immunotherapy was administered for 3 consecutive days and the radiation was performed only on day 1 at 3 Gy/dose.

Flow cytometric analysis was performed on dissociated tumor cell suspensions using PE-conjugated anti-mouse CD8a (Ly-2, eBioscience, San Diego, Calif.), FITC-conjugated anti-mouse CD4 (clone GK1.5, BioLegend, San Diego, Calif.) and TriColor anti-F4/80 monoclonal antibody (Caltag Laboratories, Burlingame, Calif.).

Tumors from each treatment group were surgically removed 72 hours post treatment initiation and single-cell homogenates were prepared. Briefly, tumors were removed, finely minced with a razor blade and incubated for 4 hours with continuous agitation in Leibovich media (Sigma-Aldrich) containing 200 U/ml collagenase (Sigma-Aldrich), 100 U/ml hyaluronidase (Sigma-Aldrich), 100 U/ml penicillin, and 100 µg/ml streptomycin. The cell suspension was filtered through a 40-µm nylon cell strainer (BD Falcon, San Jose, Calif.) into a 50 ml tube. Cells were centrifuged at 350×g for 10 minutes and the pellet was resuspended in folate-deficient RPMI media supplemented with 10% FCS and 1% antibiotics. Aliquots of cells were incubated with fluorophor labeled antibodies for CD4 and CD8 T cells and macrophages for 30 minutes at 37° C. Cells were washed three times with 1% BSA (Sigma-Aldrich) in PBS and the immunofluorescence was analyzed using a FACSscan cytometer using Cellquest software (Becton-Dickinson, Bedford, Mass.). The results are shown in the following table.

| | Treatment | | | | |
|---|---|---|---|---|---|
| | a | b | c | d | e |
| Immune cell | Percent Immune Cell Infiltration | | | | |
| CD4 T cells | 1.21 ± 0.18 | 5.68 ± 1.14 | 3.7 ± 2.56 | 12.25 ± 3.6 | 10.74 ± 1.98 |
| CD8 T cells | 6.59 ± 0.93 | 9.2 ± 0.1 | 7.64 ± 0.48 | 14.85 ± 4.34 | 6.11 ± 2.39 |
| Macrophages | 14.51 ± 2.44 | 26.26 ± 1.27 | 13.79 ± 0.98 | 31.90 ± 5.69 | 22.46 ± 1.08 |

The treatment groups are PBS (group a), immunotherapy (group b), radiation therapy with analysis of tumor 1 (group c), radiation therapy and immunotherapy with analysis of tumor 1 (group d), and radiation therapy and immunotherapy with analysis of tumor 2 (group e). The results show that there is strong infiltration of CD4 T cells, CD8 T cells, and macrophages into both the irradiated tumor (tumor 1) and the nonirradiated tumor (tumor 2).

EXAMPLE 8

Immunohistochemical Analysis of Immune Cells within Tumors

Mice bearing M109 tumors, one on the dorsal median area and the other at the base of the neck, were divided into four groups and treated as follows: (a) no treatment, (b) radiation alone, (c) folate immunotherapy, and (d) radiation plus folate immunotherapy. The folate immunotherapy was administered for 3 consecutive days and the radiation was performed only on day 1 at 3 Gy/dose.

Tumors from each experimental group were surgically removed, snap-frozen in Tissue-Tek O.C.T. compound in liquid nitrogen and sectioned at 7 μm onto Super Frost Plus slides (Fisher Scientific International). Tumor sections were fixed for 5 minutes in cold acetone, washed with 0.5% BSA in PBS and treated with 0.5% hydrogen peroxide in PBS for 10 minutes at room temperature. Nonspecific binding was blocked with 10% goat serum in PBS. Purified anti-mouse CD4 (L3T4, BD Pharmingen, Calif.), purified anti-mouse CD8a (Ly-2, BD Pharmingen, Calif.) and purified anti-mouse F4/80 (Serotec, Raleigh, N.C.) were diluted to a pre-determined optimal concentration in antibody diluent (BD Pharmingen, Calif.) and overlaid onto tumor sections. Slides were incubated in a humid chamber for 1 hour at room temperature. The slides were extensively washed with 0.5% BSA in PBS followed by incubation with biotinylated anti-rat IgG for 30 minutes at room temperature. Streptavidin-HRP (Invitrogen, Calif.) was added to each section followed by DAB reagent (Invitrogen, Calif.) as substrate for HRP. After substrate development, slides were nuclear counterstained with hematoxylin (Invitrogen, Calif.), dehydrated by passing them first through 95% alcohol and then 100% alcohol followed by xylene treatment. Mounting media was added and the sections were analyzed using an Olympus binocular microscope.

Figure 6:
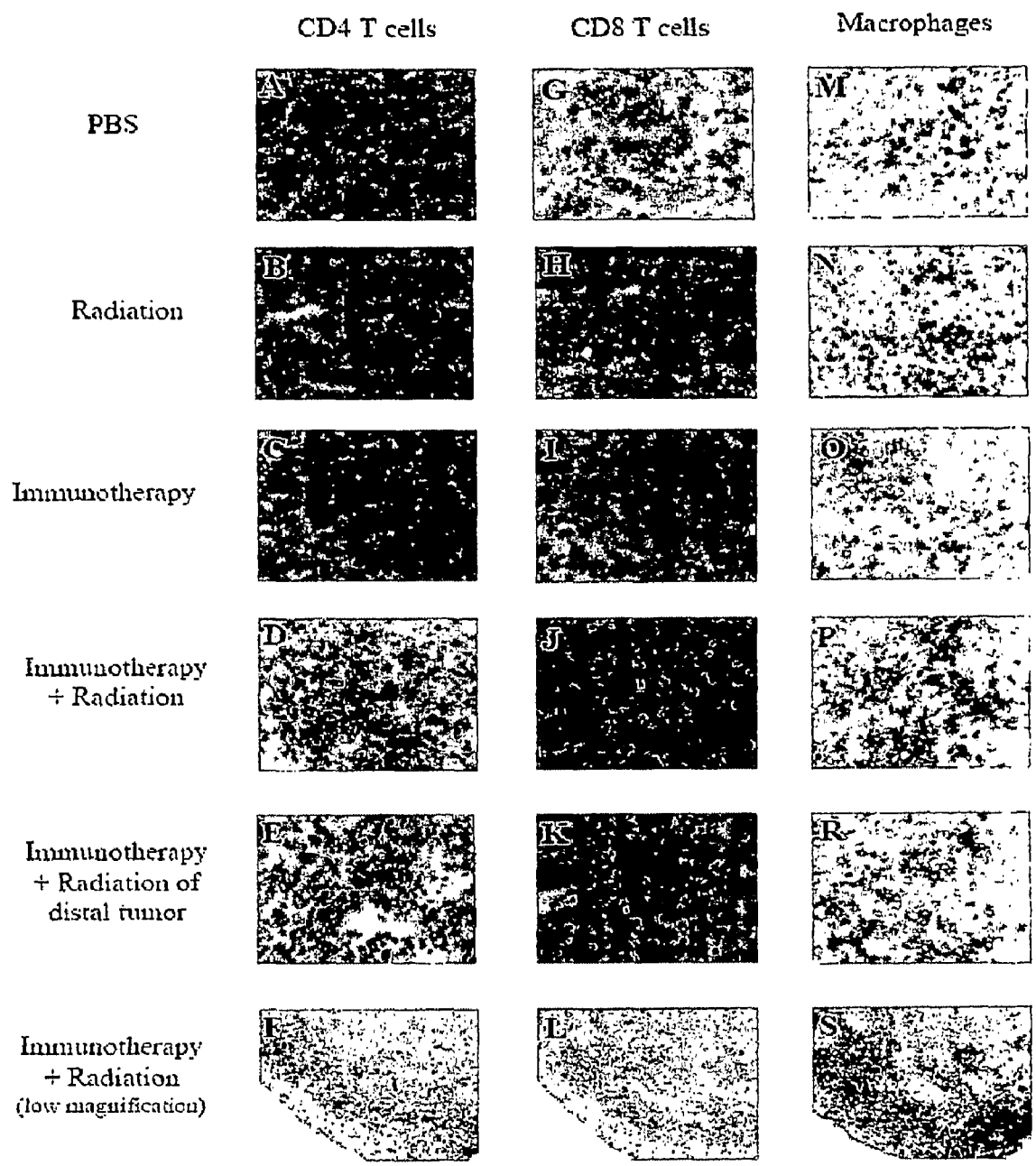
FIG. 6 shows immunohistochemical analysis of CD4 and CD8 immune cells (T cells) and macrophages within tumors for the indicated treatment groups.

The treatment groups are shown in FIG. 6. Thin sections of tumors were stained with the various antibodies described above (A-F=anti-CD4; G-L=anti-CD8; M-S=anti-F4/80). A, G, and M mice received no treatment. The B, H, and N tumor was subjected to irradiation (3 Gy) on day 1. For the C, I, and O tumor, 3 doses of immunotherapy (folate-FITC plus IL-2 and IFN-α) to the mouse was used. For the D, J, and P tumor, 3 Gy irradiation on day 1 followed by immunotherapy to the mouse was used. The E, K, and R distal tumor (nonirradiated tumor) was from a mouse where another tumor was irradiated on day 1 followed by immunotherapy to the mouse. The F, L, and S tumor was irradiated (3 Gy) on day 1 followed by immunotherapy to the mouse (lower magnification). The results show that there is strong infiltration of CD4 T cells, CD8 T cells, and macrophages into both the irradiated tumor and the nonirradiated tumor (distal tumor). The nonirradiated tumors had more immune cell infiltration than tumors exposed to either treatment alone. The majority of the tumor infiltrating immune cells were located in the outer rim of the tumors.

What is claimed is:

1. A method of enhancing an endogenous immune response-mediated elimination of a tumor in a host, the method comprising the steps of:
    administering to the host a composition comprising an immunogen conjugated to a folate or an analog or a derivative thereof,
    administering to the host a cytokine, and
    administering to the host a therapeutically effective amount of radiation wherein the amount of radiation ranges from about 0.5 to about 3 Gy per dose,
    wherein the method reduces the volume of a tumor that is present at the time of radiation and that is distant from the site of radiation.

2. The method of claim 1 wherein the folate or the analog or the derivative thereof is chemically conjugated to the immunogen through bonding comprising covalent, ionic, or hydrogen bonding.

3. The method of claim 2 wherein the bonding is covalent bonding by direct covalent bonding or by covalent bonding through a divalent linker.

4. The method of claim 1 wherein the folate or the analog or the derivative thereof has a glutamyl moiety covalently conjugated to the immunogen only via the glutamyl γ-carboxyl moiety of folate.

5. The method of claim 1 wherein the folate or the analog or the derivative thereof has a glutamyl moiety covalently conjugated to the immunogen only via the glutamyl α-carboxyl moiety of folate.

6. The method of claim 1 wherein the folate or the analog or the derivative thereof binds to a receptor that is preferentially expressed, uniquely expressed, or overexpressed on metastatic cancer cells.

7. The method of claim 1 wherein the immunogen is an organic molecule having a molecular weight less than 20,000 daltons.

8. The method of claim 1 wherein the immunogen is fluorescein or dinitrophenyl.

9. The method of claim 1 wherein the immunogen is an α-galactosyl group.

10. The method of claim 1 wherein an antibody exogenous to said host is co-administered with said conjugate composition.

11. The method of claim 1 wherein the cytokine comprises IL-2, IL-12, IL-15, or combinations thereof.

12. The method of claim 1 wherein the cytokine comprises IL-2, IL-12, IL-15, or combinations thereof, in combination with IFN-α or IFN-γ.

13. The method of claim 1 wherein the cytokine comprises IL-2, IL-12, IL-15, or combinations thereof, in combination with IFN-α or IFN-γ, or a combination thereof, and GM-CSF.

14. The method of claim 1 wherein the cytokine comprises at least one NK cell or T cell stimulant.

15. The method of claim 1 wherein the folate-immunogen conjugate composition is administered in multiple injections.

16. The method of claim 1 wherein the host had been previously exposed naturally to the immunogen so that the host has a preexisting immunity to the immunogen.

17. The method of claim 1 wherein the host had been previously exposed to the immunogen by a non-natural process resulting in priming of the host's immune response to the immunogen.

18. The method of claim 17 wherein the non-natural process resulting in priming of the immune response is vaccination.

19. The method of claim 17 wherein the non-natural process resulting in priming of the immune response is active immunization.

20. The method of claim 1 wherein the endogenous immune response comprises an humoral immune response.

21. The method of claim 20 wherein the humoral response is an acquired immune response.

22. The method of claim 21 wherein the acquired response is induced by administering to the host a vaccine composition.

23. The method of claim 20 wherein the humoral response is an innate immune response.

24. The method of claim 1 wherein the endogenous immune response comprises a cell-mediated immune response.

25. The method of claim 1 wherein the endogenous immune response comprises an humoral and a cell-mediated immune response.

* * * * *